United States Patent [19]

Shirasaki

[11] Patent Number: 4,735,213
[45] Date of Patent: Apr. 5, 1988

[54] DEVICE AND METHOD FOR DETERMINING SYSTOLIC BLOOD PRESSURE

[75] Inventor: Osamu Shirasaki, Amagasaki, Japan

[73] Assignee: Omron Tateisi Electronics Co., Kyoto, Japan

[21] Appl. No.: 898,334

[22] Filed: Aug. 20, 1986

[30] Foreign Application Priority Data

Aug. 21, 1985 [JP] Japan ................. 60-184870

[51] Int. Cl.$^4$ ............................................. A61B 5/02
[52] U.S. Cl. .................... 128/681; 128/682; 364/415
[58] Field of Search ............... 128/680–683; 364/417, 415

[56] References Cited

U.S. PATENT DOCUMENTS

| | | | |
|---|---|---|---|
| 4,271,843 | 6/1981 | Flynn | 128/681 |
| 4,427,013 | 1/1984 | Nunn et al. | 128/681 |
| 4,464,123 | 8/1984 | Glover et al. | 128/681 X |
| 4,592,365 | 6/1986 | Georgi | 128/680 |

Primary Examiner—Francis J. Jaworski
Attorney, Agent, or Firm—Wegner & Bretschneider

[57] ABSTRACT

This electronic blood pressure measurement device includes a cuff with pressurization, draining, and sensing means, a means for generating from the cuff pressure signal a pulse wave signal, and a means for determining for the patient a value for systolic blood pressure. This blood pressure determining means detects an interval during which the amplitude of the pulse wave signal increases substantially linearly, and sets the systolic blood pressure value using the pulse wave amplitude at the end of that interval. Optionally but desirably, this means locates an approximate start of the linear interval as being a point where the pulse wave amplitude has a certain relation to the pulse wave amplitude at the end of the interval, and determines the value for systolic blood pressure to be the cuff pressure at such an approximate start of the interval. The approximate start of the interval may be determined as the point where the pulse wave amplitude is a certain proportion of the pulse wave amplitude at the end of the interval; and this certain proportion may be approximately 60%. An operational method for this device is also disclosed.

4 Claims, 5 Drawing Sheets

DEVICE AND METHOD FOR DETERMINING SYSTOLIC BLOOD PRESSURE

BACKGROUND OF THE INVENTION

The present invention relates to an electronic device for measuring the blood pressure of a patient and a method of operation thereof, and more particularly relates to such a device for blood pressure measurement and such a method of operation thereof of the oscillation method type, in which the accuracy of measurement is maximized while the construction and implementation of the device are kept simple.

Generally, in the oscillation method type of blood pressure measurement device, conventionally a cuff is fitted over the arm of a patient and is inflated by a pressure pump to a pressure somewhat higher than the systolic blood pressure so as to obstruct the blood flow through the patient's arm, thereafter being deflated progressively. During the deflation process, the pressure inside the cuff is measured and a pulse wave signal is obtained therefrom.

Figure 6:
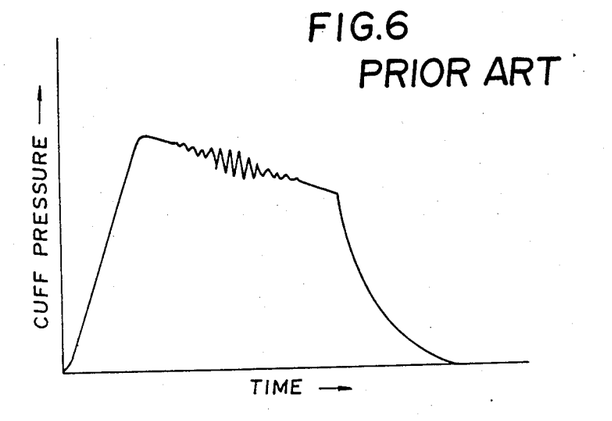
FIG. 6, which relates to the overall background of the present invention which is per se known prior art, is a graph in which time is shown along the horizontal axis and the pressure in a cuff fitted around a patient's arm is shown along the vertical axis, showing the variation of the cuff pressure during an episode of inflation and then deflation of the cuff.

In detail, the principles of the conventional or prior art method of measuring blood pressure with such a blood pressure measurement device will be now explained with reference to FIGS. 6 through 8 of the accompanying drawings. FIG. 6 is a graph in which time is shown along the horizontal axis and the pressure of the air (or other fluid) in the cuff is shown along the vertical axis, showing the variation of the cuff pressure during such an episode of inflation and then deflation of the cuff.

First of all, in the same manner as with the conventional stethoscopic method for blood pressure measurement, the cuff is fitted over the patient's arm and is then inflated with a pressure pump to a pressure somewhat higher than the systolic blood pressure (point U on the FIG. 6 graph) so as to obstruct the blood flow through the arteries in said patient's arm. Next, as the pressure in the cuff is steadily and gradually reduced by draining of the fluid from said cuff, after a certain interval a pulsation, shown in FIG. 6 as W, starts to show up in said cuff pressure, this is as a result of the pressure generated by the patient's heart and transmitted to the blood flowing in the arteries of his or her arm, said pressure being transmitted to the cuff and to the fluid therein. The frequency of this pulsation W corresponds to the frequency of the heart beat of the patient. As the cuff pressure further drops, at a certain point this cuff pressure pulsation W disappears, because the pressure on the arteries is diminished and accordingly the blood can flow more smoothly through them. Once the cuff pressure has dropped below the diastolic blood pressure of the patient, no further data can be obtained by the measurement process, and hence at the point V in FIG. 6 the cuff pressure is rapidly reduced, so as to drain the cuff completely.

Figure 7:
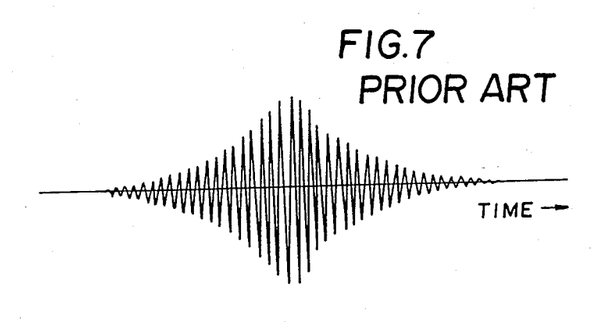
FIG. 7, which similarly relates to the overall background of the present invention, is a chart showing only a pulse wave form component W of the cuff pressure graph of FIG. 6, again with time being shown along the horizontal axis.

FIG. 7 shows only the component of the pulse wave form W described above, again with time being shown along the horizontal axis. Hereinafter, this component will be referred to as the pulse wave. And FIG. 8 shows a graph of the amplitude of this pulse wave, against time, with time being shown along the horizontal axis and the pulse wave amplitude being shown along the vertical axis.

Now, the stages of changing of this pulse wave amplitude will be described, with particular reference to FIG. 8. First, from its original substantial zero at the point A, the pulse wave amplitude increases substantially non linearly with time, i.e. with decline of cuff pressure, to a point denoted as S. Thus, the portion of this graph between the points A and S is generally concave upwards with a positive second differential coefficient. From the point S, at which substantially a sharp corner is present, so that the increase rate of the pulse wave amplitude here undergoes a relatively sharp increase, the pulse wave amplitude increases more sharply than before and now substantially linearly with time, up to a point B. From the point B, the pulse wave amplitude increases substantially non linearly with time, i.e. with decline of cuff pressure, through a maximum point denoted as M, to a point D, with the portion of this graph between the points B and D being generally concave downwards with a negative second differential coefficient. Near the point D, the pulse wave amplitude is decreasing relatively quickly with time; but at the point D substantially another sharp corner is present, so that the decrease rate of the pulse wave amplitude here undergoes a relatively sharp decrease, and thereafter the pulse wave amplitude decreases less sharply than before, down to substantially zero at the point C. And it is per se known that cuff pressure at the point S corresponds to the systolic blood pressure, while the cuff pressure at the point D corresponds to the diastolic blood pressure. The oscillation method of blood pressure measurement is based upon these principles, and has the advantage of being relatively immune to external noises, since no microphone is used, and since the frequency of the pulse wave is relatively low, being from about 0.1 Hz to about 10 Hz. In order to implement this oscillation method, there are various per se known electronic blood pressure measuring devices, such a device typically comprising: a cuff for being fitted around the arm of a patient; a means for selectively pressurizing said cuff with fluid, so as to squeeze said arm of said patient; a means for selectively draining said fluid from said cuff either at a relatively rapid rate or at a relatively slow rate; a means for sensing the pressure of said fluid in said cuff and for producing an output signal representative thereof; a means for receiving said pressure signal from said cuff pressure sensing means and for generating therefrom a signal representative of the pulse wave of the patient; and a micro processor or micro computer equipped with a determining means for determining blood pressure values according to the output signals of the pressure sensing means and of the pulse wave detecting means.

However, this type of electronic blood pressure measurement device, and the method of operation thereof, have not yet provided perfect operation. In detail, according to such an electronic blood pressure measurement device and method, the point S in the pulse wave amplitude curve is found by identifying the point at which the increase rate of the pulse wave amplitude undergoes a relatively sharp increase, i.e. the second differential coefficient of the pulse wave amplitude is substantially discontinuous, and the cuff pressure corresponding to this point S is determined as being the systolic blood pressure; but, in an actual pulse wave amplitude curve, the point S at which the pulse wave amplitude thus begins a sharp rise may not be so easy to establish precisely, because it is not always so completely clear and well defined as may appear from the foregoing discussion. Accordingly, the reliability of the measured blood pressure may not be sufficiently high.

Further, the sharp of the blood pressure wave form of the patient, and the corresponding shape of the pulse wave amplitude curve, cannot be accurately predicted in advance, because of variation of the measurement conditions and because of individual differences between patients which can be very substantial. The problem thus arises that, if a micro computer program is to be implemented which can accurately determine blood pressure values in spite of such large variations in individual cases in the shape of the pulse wave amplitude curve, the program tends to be so large and voluminous and intricate that the development and debugging of such massive program becomes very difficult. Furthermore, the memory size of the micro computer may not be adequate to the task of storage of the program and/or all the data required therefor, and problems may also arise with regard to the speed of operation of the microcomputer, and sharp increase may occur in the processing time.

SUMMARY OF THE INVENTION

Figure 8:
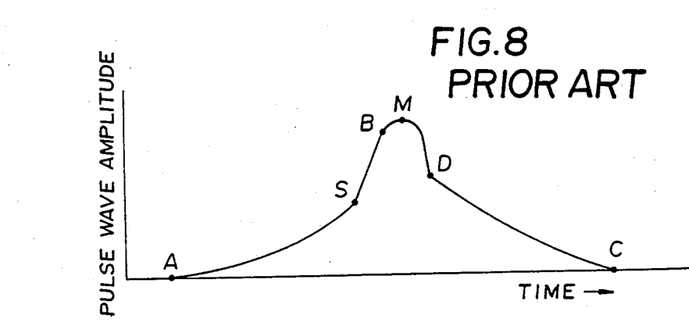
FIG. 8, which also similarly relates to the overall background of the present invention, is a graph showing the amplitude of this pulse wave component against time, with time again being shown along the horizontal axis and the pulse wave component amplitude being shown along the vertical axis.

The inventor of the present invention considered the various problems detailed above with relation to location of the point B on the FIG. 8 graph for determination of the systolic blood pressure, from the point of view of the desirability of minimizing memory size and processing time requirements for the micro computer, as well as of minimizing the complexity of the control program therefor.

Accordingly, it is the primary object of the present invention to provide an electronic blood pressure measurement device of the continuous measurement type, which avoids the problems detailed above.

It is a further object of the present invention to provide such an electronic blood pressure measurement device, the program for the micro computer incorporated in which is not required to be extremely complex.

It is a further object of the present invention to provide such an electronic blood pressure measurement device, the micro computer incorporated in which is not required to have an extremely large store or to be very fast.

It is a further object of the present invention to provide such an electronic blood pressure measurement device, which maintains good measurement accuracy.

It is a further object of the present invention to provide such an electronic blood pressure measurement device, which is relatively simple to manufacture.

It is a further object of the present invention to provide such an electronic blood pressure measurement device, which is cheap to build.

It is a yet further and concomitant object of the present invention to provide a method of operating such an electronic blood pressure measurement device, which aids with the resolution of the above identified problems, and others.

The basic idea of the present invention is that, rather than directly determining the point S of FIG. 8 by determining the point at which the second derivative of said curve is substantially discontinuous, i.e. at which the curve angles through an upwardly concave corner, and rather than trying to directly find the starting point of a linear interval which might be prone to error due to spurious linear portions in the portion of said curve from the point A to the point S, instead the point B is determined as the end of the substantially linear interval from the point S to the point B, and then the timing of the point S is approximately determined, according to the pulse wave amplitude at the point B.

According to the most general device aspect of the present invention, the above and other objects are attained by an electronic blood pressure measurement device, comprising: (a) a cuff for being fitted around the arm of a patient; (b) a means for selectively pressurizing said cuff with fluid, so as to squeeze said arm of said patient; (c) a means for selectively draining said fluid from said cuff either at a relatively rapid rate or at a relatively slow rate; (d) a means for sensing the pressure of said fluid in said cuff and for producing an output signal representative thereof; (e) a means for receiving said pressure signal from said cuff pressure sensing means and for generating therefrom a signal representative of the pulse wave of the patient; and: (f) a blood pressure determining means for determining for the patient a value for systolic blood pressure, by detecting an interval during which the amplitude of said pulse wave signal increases in a substantially linear manner, and by setting said systolic blood pressure value using the pulse wave amplitude at the end of said interval; and, according to the most general method aspect of the present invention, these and other objects are attained by a method for operating an electronic blood pressure measurement device comprising: (a) a cuff for being fitted around the arm of a patient; (b) a means for selectively pressurizing said cuff with fluid, so as to squeeze said arm of said patient; (c) a means for selectively draining said fluid from said cuff either at a relatively rapid rate or at a relatively slow rate; (d) a means for sensing the pressure of said fluid in said cuff and for producing an output signal representative thereof; and: (e) a means for receiving said pressure signal from said cuff pressure sensing means and for generating therefrom a signal representative of the pulse wave of the patient; wherein an interval is detected in which the amplitude of said pulse wave increases in a substantially linear manner, and a systolic blood pressure value for the patient is set using the pulse wave amplitude at the end of said interval.

According to such a device and such an operational method therefor as specified above, since the linear interval from the point S to the point B can be identified without fail even when its exact starting point S at which the pulse wave amplitude begins its sudden increase is somewhat indistinct, and since finding the end point B of such a linear interval is both simple and can be relied upon, therefore a reliable and reasonably accurate value for the systolic blood pressure of the patient can be determined, as will become clear from the following descriptions.

Further, according to particular specializations of the device aspect of the present invention, the above specified and other objects are more particularly attained by an electronic blood pressure measurement device as described above, wherein said blood pressure determining means comprises a means for locating an approximate start of said interval as a point where the pulse wave amplitude has a certain relation to the pulse wave amplitude at the end of said interval, and further comprises a means for determining the value for the patient's systolic blood pressure to be the cuff pressure at said approximate start of said interval; and optionally said means for locating an approximate start of said interval may determine said approximate start of said interval as the point where the pulse wave amplitude is a certain proportion of the pulse wave amplitude at the end of said interval; and, further optionally, said certain proportion of the pulse wave amplitude at the end of said interval may be approximately 60% thereof. Similarly, according to particular specializations of the method aspect of the present invention, the above specified and other objects are more particularly attained by a method for operating an electronic blood pressure measurement device as described above, wherein an approximate start of said interval is determined as a point where the pulse wave amplitude has a certain relation to the pulse wave amplitude at the end of said interval, and further the value for the patient's systolic blood pressure is determined to be the cuff pressure at said approximate start of said interval and optionally said approximate start of said interval may be determined as the point where the pulse wave amplitude is a certain proportion of the pulse wave amplitude at the end of said interval and, further optionally, said certain proportion of the pulse wave amplitude at the end of said interval may be approximately 60% thereof.

BRIEF DESCRIPTION OF THE DRAWINGS

The present invention will now be described with respect to the preferred embodiments of the device and of the method thereof, and with reference to the illustrative drawings appended hereto, which however are provided for the purposes of explanation and exemplification only, and are not intended to be limitative of the scope of the present invention in any way, since this scope is to be delimited solely by the accompanying claims. With relation to the figures, spatial terms are to be understood as referring only to orientation on the drawing paper, unless otherwise specified; like reference numerals, unless otherwise so specified, denote the same parts and gaps and spaces and so on in the various figures; and:

DESCRIPTION OF THE PREFERRED EMBODIMENTS

Figure 1:
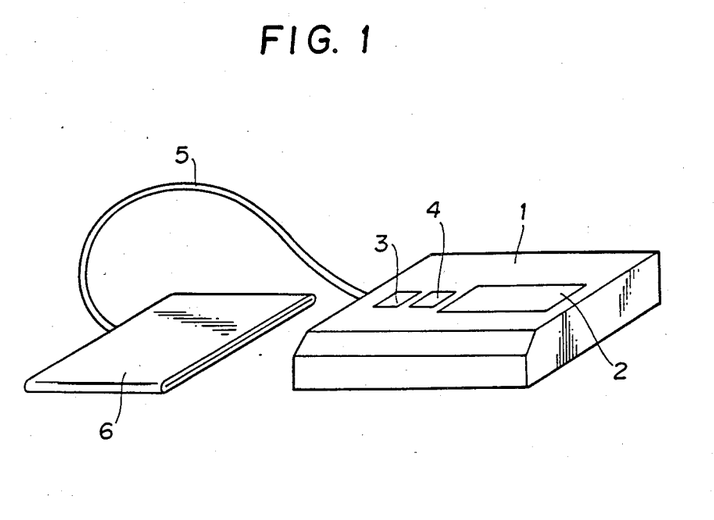
FIG. 1 is a perspective view of the preferred embodiment of the electronic blood pressure measurement device of the present invention, which performs the preferred embodiment of the electronic blood pressure measurement device method of operation of the present invention.

The present invention will now be described with reference to the preferred embodiments of the device and of the method thereof, and with reference to the figures. In FIG. 1, a general perspective view, and in FIG. 2 a schematic overall block diagram, of said preferred embodiment of the electronic blood pressure measurement device of the present invention are shown. In these figures, the reference numeral 1 denotes the main body of the blood pressure measurement device, on the upper face of which are mounted a display unit 2 which may be a liquid crystal (LCD) type display, a power switch 3, and a measurement initiation switch 4. A flexible tube 5, which may be made of rubber or the like, is connected between said electronic blood pressure measurement device main body 1 and a cuff 6 of a per se known type, adapted for being fitted around the arm of a patient and for being selectively inflated and deflated, either to squeeze said patient's arm or to release it.

Figure 2:
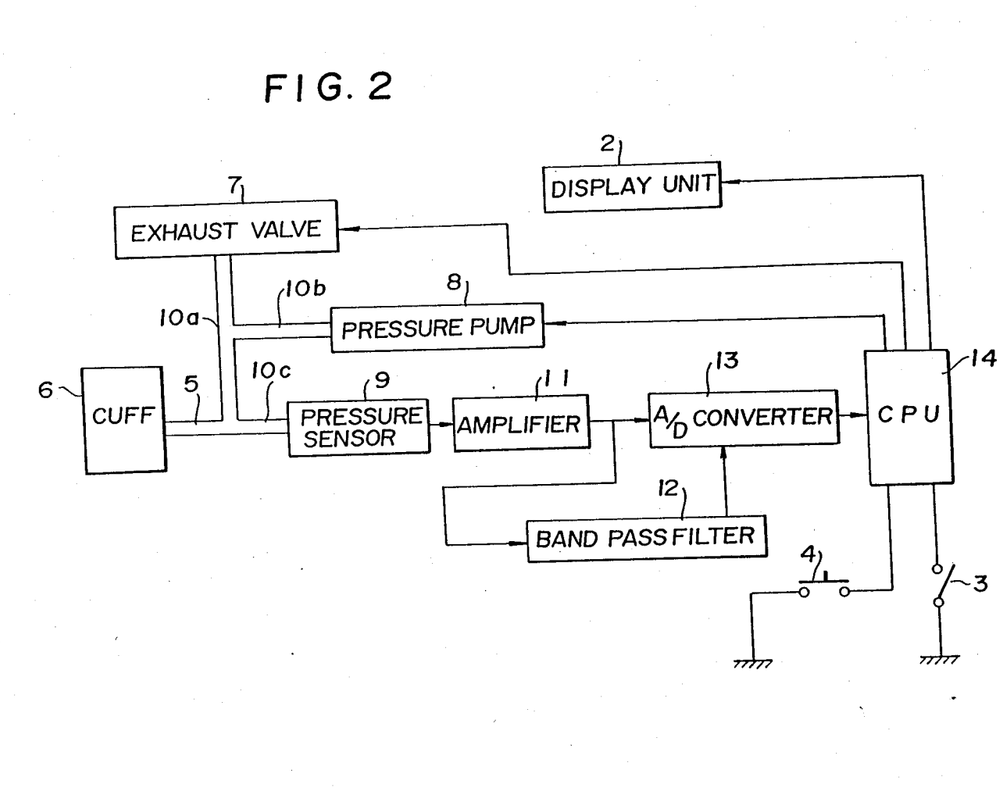
FIG. 2 is a schematic block diagram of said preferred device embodiment for performing said preferred method embodiment.

Referring to FIG. 2 which shows the internal details of this electronic blood pressure measurement device, there are comprised therein an exhaust valve 7 and a pressure pump 8 which are connected to the tube 5 leading to the cuff 6 via respective tubes 10a and 10b, and an air pressure sensor 9 which is connected to said tube 5 leading to the cuff 6 by way of a tube 10c. This air pressure sensor 9 outputs an electronic signal indicating the pressure level of the air in the cuff 6. These tubes 10a, 10b, and 10c, and the exhaust valve 7, the pressure pump 8, and the air pressure sensor 9, are provided internally to the main body 1 of the electronic blood pressure measurement device. The exhaust valve 7, in more detail, comprises an electromagnetic solenoid valve which opens and closes at a relatively rapid rate at a certain duty factor, so as to be able to drain the air pressure from the cuff 6 either at a relatively slow rate or at a relatively rapid rate, according to the duty ratio of a control signal supplied to said electromagnetic solenoid valve from a micro computer (CPU) 14 which will be described hereinafter; however, alternative arrangements are also possible for this exhaust valve 7, as long as it provides the above described functionality.

Now, the circuitry for measurement and control incorporated in this electronic blood pressure measurement device will be described. The output signal from the air pressure sensor 9 is fed to the input of an amplifier 11, the output of which on the one hand is directly connected to a first input side of an A/D converter 13, and on the other hand is connected to a second input side of said A/D converter 13 via a band pass filter 12, which acts as a pulse wave component detecting means which detects the pulse wave component of the output from the pressure sensor 9. Thus, one of the input sides of said A/D converter 13 receives a static pressure value from the amplifier 11 representing the pressure in the cuff 6, while the other input side of said A/D converter 13 receives, via the band pass filter 12, a value representing the pulse wave component of said pressure in said cuff 6.

The output side of the A/D converter 13 is connected to an input of a CPU (central processing unit) 14 which typically is a microcomputer incorporating an microprocessor, and thereby digitalized data representing cuff pressure and the aforementioned pulse wave signal are fed to said CPU 14.

Within the CPU 14, there are provided various typical and per se conventional microcomputer components such as RAM (random access memory), ROM (read only memory), and so on; and this CPU performs the functions of determining values representing a systolic blood pressure, an average blood pressure, and a diastolic blood pressure of the patient. These various calculations are performed by the CPU 14, based upon a program stored in its ROM, and keeping data values in its RAM. Then the CPU 14 displays on the display unit 2 the numerical values of said systolic, average, and diastolic blood pressures. And the CPU 14 further is connected to the power switch 3 and to the measurement initiation switch 4; also, said CPU 14 selectively outputs an electronic signal so as to control the pressure pump 8, either to operate said pump 8 or to stop said pump 8; and, similarly, said CPU 14 selectively outputs an electronic signal so as to control the exhaust valve 7, either to operate said exhaust valve 7 at a relatively high venting speed or to operate said exhaust valve 7 at a relatively low venting speed.

Now, the detailed action and operation of this preferred embodiment of the electronic blood pressure measurement device of the present invention, according to the preferred embodiment of the electronic blood pressure measurement device operating method of the present invention, will be described, with reference to the flow charts for fragments of the program obeyed by the CPU 14 incorporated therein shown in FIGS. 3, 4, and 5.

Figure 3:
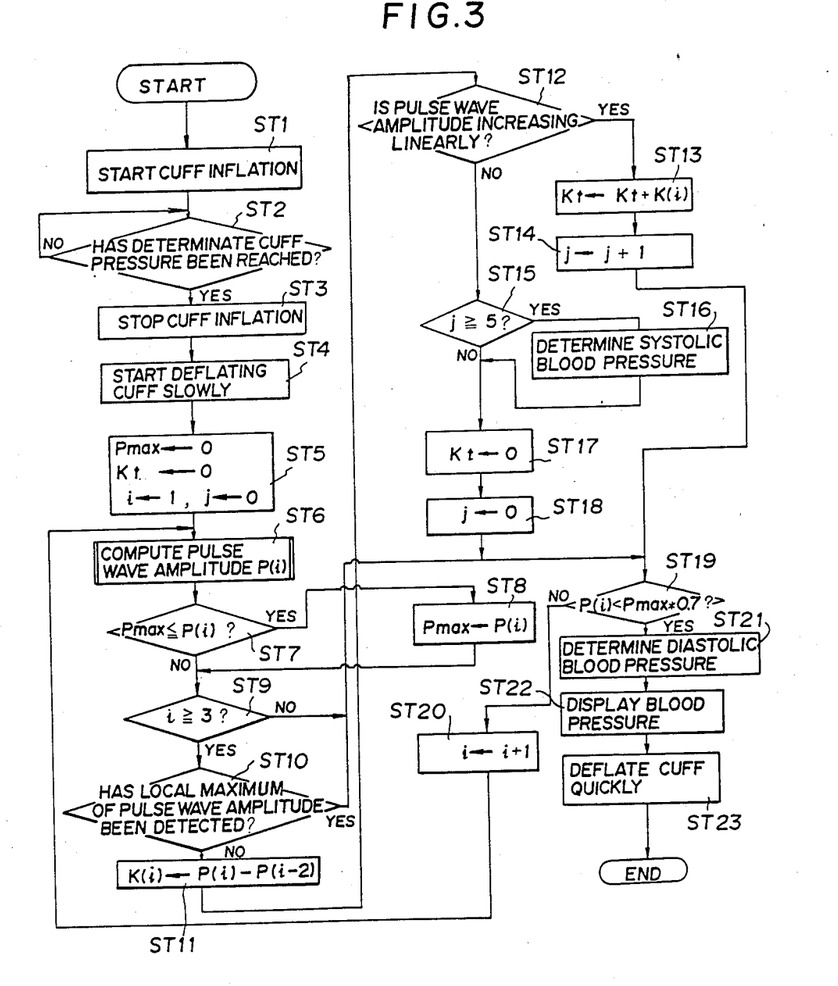
FIG. 3 is a flow chart illustrating the flow of the main fragment of a program which is stored in and obeyed by a microprocessor or CPU incorporated in said preferred embodiment of the electronic blood pressure measurement device of the present invention.

Referring first to the main or overall flow chart shown in FIG. 3, first of all, as a preparatory step, the cuff 6 is fitted around the arm of the patient, and the power switch 3 is turned on. Next, the measurement initiation switch 4 is similarly turned on, which starts the operation of the CPU 14. Thus, the action of said CPU 14 in obeying its stored program starts at the START box of FIG. 3. Next, in the step ST1, the CPU 14 starts the action of the pressure pump 7 and supplies compressed air into the cuff 6, so as to inflate it and so as to squeeze the arm of the patient. Next, the flow of control passes to the decision step ST2.

In this decision step ST2, each sample time, a decision is made as to whether the pressure in the cuff 6 has yet risen far enough to have attained a determinate pressure value, or not, according to the signal which the CPU 14 receives from the pressure sensor 9 via the amplifier 11 and the A/D converter 13. This determinate pressure value is generally set to be greater than the maximum blood pressure that can occur in practice. If the answer to this decision is NO, so that the pressure in the cuff 6 is less than said determinate pressure value, then it is deemed that further cuff inflation is required, and then the flow of control passes back to this step ST2 again, to continue the inflation of the cuff 6. On the other hand, if the answer to this decision is YES, so that the pressure in the cuff 6 has now risen up to said determinate pressure value, then it is deemed that no further cuff inflation is currently required, and in this case the flow of control passes next to the step ST3.

In this step ST3, the inflation of the cuff is stopped, by the CPU 14 outputting an appropriate OFF signal to the pressure pump 8 so as to cause said pressure pump 8 to stop its operation; and next the flow of control passes to the step ST4.

In this step ST4, gradual venting of the air in the cuff 6 via the exhaust valve 7 is commenced, by the CPU 14 outputting an appropriate signal to said exhaust valve 7, so that the cuff pressure starts steadily dropping; and next the flow of control passes to the step ST5.

In this step ST5, the CPU 14 initializes variables $P_{max}$ and $K_t$, and sets a control variable j to zero and another control variable i to unity; and next the flow of control passes to the step ST6.

In this next step ST6, which is within a cycle which will be explained shortly, the CPU 14 computes the pulse wave amplitude of the i-th pulsation from the digital signal of the pulse wave component of the output of the A/D converter 13, and stores the value in its memory (such as RAM memory) as P(i). Next, the flow of control passes to the decision step ST7.

In this decision step ST7, a decision is made as to whether the current value of $P_{max}$, the maximum value so far found for the pulse wave amplitude, is less than or equal to this value P(i), or not. If the answer to this decision is YES, so that $P_{max}$ is in fact not greater than P(i), then it is appropriate to update $P_{max}$ to this new maximum value, and then the flow of control passes next to the step ST8. On the other hand, if the answer to this decision is NO, so that $P_{max}$ is in fact already greater than P(i), then it is deemed that no updating of $P_{max}$ is necessary, and in this case the flow of control passes next directly to the decision step ST9, bypassing the step ST8. And, in the step ST8, the current value of P(i) is assigned to $P_{max}$, and next the flow of control passes to the same decision step ST9.

In this decision step ST9, a decision is made as to whether the value of i is greater than or equal to 3, or not. If the answer to this decision is NO, so that i is in fact less than 3, then the flow of control passes next to the step ST19 which will be described hereinafter, because certain steps from ST10 onwards cannot be performed if i is less than 3, i.e. is equal to 1 or to 2. On the other hand, if the answer to this decision is YES, so that i is in fact greater than or equal to 3, then it is acceptable to proceed, and in this case the flow of control passes next to the decision step ST10.

In this decision step ST10, a decision is made as to whether a local maximum of the pulse wave amplitude has been detected, or not. If the answer to this decision is YES, so that a local maximum of the pulse wave amplitude has in fact been detected, then it is appropriate to advance to a phase of the calculation for determination of a value for the diastolic blood pressure, and then as before the flow of control passes next to the step ST19. On the other hand, if the answer to this decision is NO, so that a local maximum of the pulse wave amplitude has not in fact been detected, then it is deemed that it is appropriate to calculate a value for the systolic blood pressure as will be described in the following steps, and in this case the flow of control passes next to the step ST11.

In this step ST11, the difference between the current pulse wave amplitude P(i) and the pulse wave amplitude P(i−2) two cycles back is computed (this is for determining whether a linear increase is occurring or not), and the value is set as K(i). Next, the flow of control passes to the decision step ST12.

In this decision step ST12, a decision is made as to whether the pulse wave amplitude is increasing linearly, or not. The manner in which this is decided will be explained hereinafter. If the answer to this decision is YES, so that in fact the pulse wave amplitude is increasing linearly, then it is deemed that the process has entered and is still within the interval of linear increase between the points S and B as illustrated in FIG. 8, and then the flow of control passes next to the step ST13. On the other hand, if the answer to this decision is NO, so that the pulse wave amplitude is not now increasing linearly, then it is deemed that the process has passed past the point B as illustrated in FIG. 8, and in this case the flow of control passes next to the step ST15; this case will be described shortly.

Now assume that the process has entered and is still within the interval of linear increase between the points S and B as illustrated in FIG. 8. In the step ST13, which is reached as explained above if and only if it is decided in the decision step ST12 that the pulse wave amplitude is increasing linearly, the value of K(i) mentioned earlier is added to the value of $K_t$, the value of j is incremented, and next the flow of control passes to the decision step ST19. The variable or counter j is thus counted up from zero upon start of the interval of linear increase.

Thus, in this next decision step ST19, a decision is made as to whether the current P(i) is smaller than 0.7 times the maximum value $P_{max}$, or not. This process is for determining the diastolic blood pressure, and, since $P(i) < 0.7*P_{max}$ never holds as long as P(i) is increasing, in this case the answer to this decision is NO, and then the flow of control passes next to the step ST20. On the other hand, if the answer to this decision were to be YES, then in such a case the flow of control would pass next to the step ST21. In the step ST20, the value of i is incremented, and next the flow of control passes back to the step ST6 again, thus to loop. Thus, under the above assumption that the process has entered and is still within the interval of linear increase between the points S and B as illustrated in FIG. 8, the processes in the steps ST6 through ST14 and ST19 and ST20 and back to the step ST6 again are repeated.

On the other hand, when the process passes the point B as illustrated in FIG. 8, the decision in the decision step ST12 becomes a NO decision, so that it is determined that the interval of linear increase of the pulse wave amplitude is over, and in such a case the flow of control is passed to the decision step ST15. In this decision step ST15, a decision is made as to whether the value of the count variable j is greater than or equal to 5, or not. If the answer to this decision is NO, so that j is currently less than 5, then the flow of control passes next to the step ST17, skipping the step ST16. On the other hand, if the answer to this decision is YES, so that j is greater than or equal to 5, then it is deemed that, and in this case the flow of control passes next to the step ST16. In this step ST16, a value is determined for the systolic blood pressure, in a manner which will be described hereinafter; and next the flow of control passes to the step ST17. The systolic blood pressure is not determined if j is less than 5, because an actual pulse wave curve may not in practice be so clean as exemplarily shown in FIG. 8, and small (although atypical) intervals of linear increase may actually exist even between the points A and S or between the points B and C. As for the interval of linear increase between the points S and B, since it has experimentally been determined that this will surely continue for at least five pulse cycles, by as above determining a value for the systolic blood pressure only when j is greater than or equal to 5, the possibility of wrongly determining a value for the systolic blood pressure due to such a small maverick interval of linear increase in some other area of the FIG. 8 graph is eliminated. If in fact a systolic blood pressure value is determined in the step ST16, it is stored in the RAM memory of the CPU 14.

In the next step ST17, the value of $K_t$ is reset to zero again, and next the flow of control passes to the step ST18, in which the value of j is reset to zero again. Next, the flow of control is passed to the decision step ST19, as before in the other branch from the decision step ST12, and the cycle back to the step ST6 via said decision step ST19 and the step ST20 is recommenced.

Thus, even when a systolic blood pressure value has been determined in the step ST16 and this systolic blood pressure value has been stored, the values of $K_t$ and j are reset to zero again in the steps ST17 and ST18 so as to be ready for the appearance of the next interval of linear increase, because an interval of linear increase in which five or more pulse cycles occur may exist, in addition to the above mentioned short intervals of linear increase, in the interval between the points A and S of the pulse wave amplitude curve of FIG. 8. If this should happen, it should be possible to determine the systolic blood pressure again in the interval between the points S and B. Therefore, the value for the systolic blood pressure which is stored in the memory of the CPU 14 is the value which was determined in the currently latest interval of linear increase (with j greater than or equal to 5).

As the pulse wave amplitude starts decreasing in the region beyond the point M on the pulse wave amplitude curve of FIG. 8, then the test of the step ST7 as to whether $P_{max}$ was less than or equal to P(i) or not gives a NO result, and the flow of control will advance to the step ST9 without updating the value of $P_{max}$. Thus, in the subsequent process steps, the value stored as $P_{max}$ is the pulse wave amplitude value at the point M on the pulse wave amplitude curve of FIG. 8. The steps of ST6 and ST7, ST9 through ST12, ST17 through ST20, and then ST6 and so on again, are repeated until P(i) detected in the step ST6 becomes such that $P(i) < 0.7*P_{max}$ for the first time holds, in the decision step ST19.

When this happens, in other words the comparison of the step ST19 gives a YES result, then the flow of control is passed to the step ST21. In this step ST21, a value is determined for the diastolic blood pressure. This is done by storing the value of the cuff pressure at this time when $P(i) < 0.7*P_{max}$ holds into the memory of the CPU 14 as the diastolic blood pressure. This is done because it has been determined by experience and experiment that the point D of the pulse wave amplitude curve of FIG. 8 is located at approximately 70% of the maximum pulse wave amplitude (the point M). Next the flow of control passes to the step ST22.

In this step ST22, the currently determined values for the systolic blood pressure, the average blood pressure, and the diastolic blood pressure are displayed on the display unit 2 therefor; and next the flow of control passes to the step ST23.

In this step ST23, high speed venting of the air in the cuff 6 via the exhaust valve 7 is commenced, by the CPU 14 outputting an appropriate signal to said exhaust valve 7, so that the cuff pressure starts steadily and quickly dropping; and next the flow of control passes to the end of this FIG. 3 routine, via the END block thereof.

Figure 4:
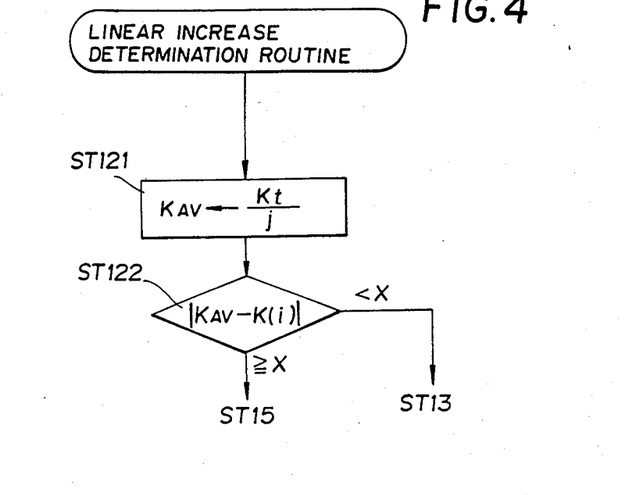
FIG. 4, similarly to FIG. 3, is a flow chart illustrating the flow of another program fragment stored in and obeyed by said microprocessor CPU, said program fragment being a routine included in the main program flow for determining whether or not an interval of linear increase of pulse wave amplitude is currently occurring.

In the flow chart of FIG. 4, there is shown the flow of another program fragment stored in and obeyed by the CPU 14, said program fragment incorporating the details of the above described determination in the step ST12 of the FIG. 3 flow chart as to whether or not an episode of linear increase of the pulse wave amplitude is occurring. This routine operates as follows.

First, in the step ST121, the average value $K_{AV}$ of K(i) is derived by dividing the current value of $K_t$ by the value of the control variable j or the number of additions in the step ST13; and next the flow of control passes to the decision step ST122.

In this decision step ST122, a decision is made as to whether the absolute value of the difference between $K_{AV}$ and the current value of K(i) is less than a determinate value X, or not. If the answer to this decision is YES, so that K(i)<X, then it is deemed that an interval of linear increase of the pulse wave amplitude is currently occurring, and then the flow of control passes next to the step ST13. On the other hand, if the answer to this decision is NO, so that K(i)>=X, then it is deemed that an interval of linear increase of the pulse wave amplitude is not currently occurring, and in this case the flow of control passes next to the step ST15.

By completion of the above FIG. 4 routine, the flow of control completes the action shown in FIG. 3 only by the decision block ST12, and next the flow of control passes to the step ST13 or the step ST15, as appropriate.

Figure 5:
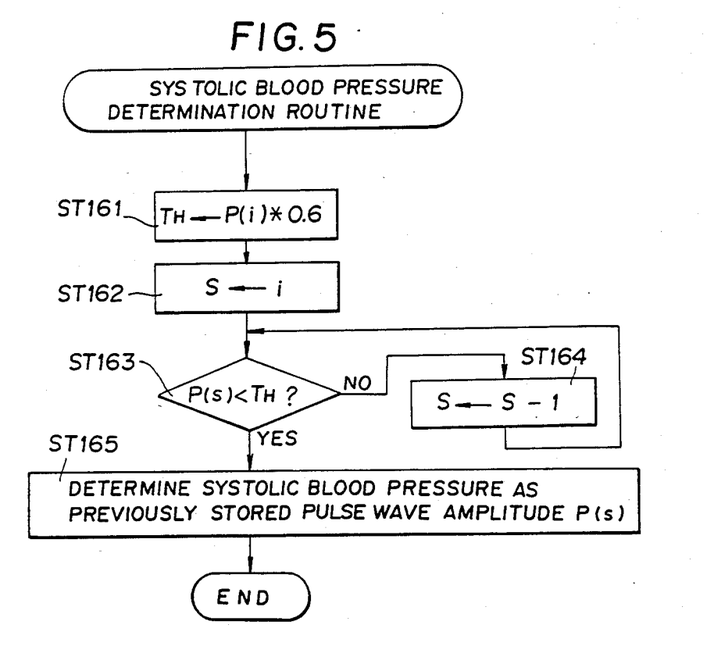
FIG. 5, similarly to FIGS. 3 and 4, is a flow chart illustrating the flow of another program fragment stored in and obeyed by said microprocessor CPU, said program fragment being a routine included in the main program flow for determining a value for the patient's systolic blood pressure.

In the flow chart of FIG. 5, there is shown the flow of another program fragment stored in and obeyed by the CPU 14, and corresponding to this step ST16, said program fragment incorporating the details of the above described determination of the systolic blood pressure. This routine operates as follows.

First, in the step ST161, a threshold value $T_H$ is calculated as being 0.6 times the value of the current pulse wave amplitude P(i), and next the flow of control passes to the step ST162.

In this step ST162, a control variable S is set to the value of the variable i. Next, the flow of control passes to the decision step ST163.

In this decision step ST163, a decision is made as to whether the pulse wave amplitude value P(s) is less than the threshold value $T_H$, or not. If the answer to this decision is NO, so that this pulse wave amplitude value P(s) is greater than or equal to said threshold value $T_H$, then it is deemed that another previous pulse wave amplitude value P(s) should be tried, and then the flow of control passes next to the step ST164. On the other hand, if the answer to this decision is YES, so that indeed at this time the pulse wave amplitude value P(s) is less than the threshold value $T_H$, then in this case the flow of control passes next to the step ST165.

In the step ST164, the value of S is decremented, so as to try the previous P(s) value; and next the flow of control passes back to return to the step ST163, to loop round again.

On the other hand, in the step ST165, it is determined that a value has been found for s at which the pulse wave amplitude value P(s) was less than the threshold value $T_H$, so that next the value of the cuff pressure which corresponded to this previous index value P(s) is read out from the memory of the CPU 14, and, after storing this value as the value for the patient's systolic blood pressure, next the flow of control passes to the end of this FIG. 5 routine, via the END block thereof. It should be noted that in the step ST6 of the main routine shown in FIG. 3 every time the pulse wave amplitude P(i) is measured its value is stored in the memory of the CPU 14, although this fact is not explicitly mentioned above or shown in the FIG. 3 flow chart.

By completion of the above FIG. 5 routine, the flow of control completes the action shown in FIG. 3 only by the block ST16, and next the flow of control passes to the step ST17.

According to such a device and such an operational method therefor as specified above, since the linear interval from the point S to the point B can be identified without fail even when its exact starting point S at which the pulse wave amplitude begins its sudden increase is somewhat indistinct, and since finding the end point B of such a linear interval is both simple and can be relied upon, therefore a reliable and reasonably accurate value for the systolic blood pressure of the patient can be determined. And, according to the present invention as described above, the complexity required for the program of the CPU 14 is not excessive, and memory requirements as well as operational speed requirements for said CPU 14 do not at all exceed those currently available with a common and cheap microprocessor.

Although the present invention has been shown and described in terms of the preferred embodiment thereof, and with reference to the appended drawings, it should not be considered as being particularly limited thereby, since the details of any particular embodiment, or of the drawings, could be varied without, in many cases, departing from the ambit of the present invention. The means and method for determining the diastolic blood pressure value are not to be considered as being limited to the means disclosed with relation to these preferred embodiments of the present invention, because it would also be possible, alternatively, to determine the diastolic blood pressure in an analogous manner to the manner in which the systolic blood pressure was determined, i.e. by detecting an end point of the interval of linear decrease of the pulse wave amplitude and by setting the diastolic blood pressure as the pulse wave amplitude at the end of this linear decrease interval. Other possibilities could also be implemented. Further, although in the step ST161 described above the threshold value $T_H$ was set as 0.6 times the pulse wave amplitude value P(i), in other possible embodiments alternative settings could be employed. Also, although in the step ST6 of the main routine of FIG. 3 of the disclosed preferred embodiments the maximum pulse wave amplitude was set as P(i) over only one cycle of the pulse wave, it would alternatively be possible to divide the lapse time of the measurement into equal intervals and to determine the maximum value of the pulse wave amplitude in the i-th interval as P(i) (the so called "window" method). Yet further, although in the above described preferred embodiments of the present invention the exhaust valve 7 and the pressure pump 8 were automatically controlled by the CPU 14, this is not to be considered as being limitative of the present invention, and they could alternatively be manually controlled, without departing from the principles of the present invention. Accordingly, the scope of the present invention is to be considered as being delimited, not by any particular perhaps entirely fortuitous details of the disclosed preferred embodiment, or of the drawings, but solely by the scope of the accompanying claims, which follow.

What is claimed is:

1. An electronic blood pressure measurement device, comprising:
    (a) a cuff means for being fitted around the arm of a patient;
    (b) a means for selectively pressurizing said cuff means with fluid, so as to squeeze said arm of said patient;
    (c) a means for selectively draining said fluid from said cuff means either at a relatively rapid rate or at a relatively slow rate;
    (d) a means for sensing the pressure of said fluid in said cuff means and for producing a pressure output signal representative thereof;
    (e) a means for receiving said pressure output signal from said cuff pressure sensing means and for generating therefrom An Associated pulse wave signal representative of the pulse wave of the patient; and
    (f) a blood pressure determining means for receiving said pressure output signal and said pulse wave signal and for determining for the patient a value for systolic blood pressure as a blood pressure measurement, said blood pressure determining means comprising means for determining an interval during which the amplitude of said pulse wave signal changes in a substantially linear manner and a higher amplitude end of said interval, and means for setting said systolic blood pressure value at a value corresponding to that pressure output signal associated with a pulse wave signal amplitude which is a fraction of the pulse wave signal amplitude at said end of said interval.

2. An electronic blood pressure measurement device according to claim 1, wherein said fraction is approximately six tenths.

3. A method for operating an electronic blood pressure measurement device comprising the step of:
    (a) fitting a cuff around an arm of a patient;
    (b) selectively pressurizing said cuff with fluid, so as to squeeze said arm of said patient;
    (c) selectively draining said fluid from said cuff either at a relatively rapid rate or at a relatively slow rate;
    (d) sensing the pressure of said cuff and producing an output signal representative thereof;
    (e) receiving said output signal respresentative of pressure from said cuff and generating therefrom an associated signal representative of the pulse wave of said patient;
    (f) determining an interval in which the amplitude of said pulse wave signal changes in a substantially linear manner and a higher amplitude of end of said interval, and
    (g) setting a systolic blood pressure value as a blood pressure measurement for the patient at a value corresponding to that pressure output signal associated with a pulse wave signal amplitude which is a fraction of the pulse wave signal amplitude at said end of said interval.

4. A method for operating an electronic blood pressure measurement device according to claim 3, wherein said fraction is approximately sixtenth.

* * * * *